US012605067B2

(12) United States Patent　　(10) Patent No.:　US 12,605,067 B2
Boland　　(45) Date of Patent:　Apr. 21, 2026

(54) OPTICAL ELEMENT MOVEMENT MECHANISM FOR MULTI-MODALITY OPHTHALMIC IMAGING SYSTEMS

(71) Applicant: Optos plc, Scotland (GB)

(72) Inventor: Estelle Boland, Dunfermline (GB)

(73) Assignee: Optos plc, Dunfermline (GB)

( * ) Notice: Subject to any disclaimer, the term of this patent is extended or adjusted under 35 U.S.C. 154(b) by 335 days.

(21) Appl. No.: 18/527,603

(22) Filed: Dec. 4, 2023

(65) Prior Publication Data

US 2024/0180422 A1　　Jun. 6, 2024

(30) Foreign Application Priority Data

Dec. 5, 2022　(EP) ..................................... 22211420

(51) Int. Cl.
*A61B 3/14*　　(2006.01)
(52) U.S. Cl.
CPC ....................................... *A61B 3/14* (2013.01)
(58) Field of Classification Search
CPC ....................................................... A61B 3/14
See application file for complete search history.

(56) References Cited

U.S. PATENT DOCUMENTS

2002/0091323 A1　7/2002　Dreher
2015/0070655 A1　3/2015　Rossi

FOREIGN PATENT DOCUMENTS

| EP | 0045897 A2 | 2/1982 |
| JP | 08-322798 A | 12/1996 |
| JP | 10-118023 A | 5/1998 |
| JP | 2001-245851 A | 9/2001 |
| JP | 2002-516688 A | 6/2002 |
| JP | 7124318 B2 | 8/2022 |
| WO | 2014/053824 A1 | 4/2014 |

OTHER PUBLICATIONS

European Search Report for EP Patent Application No. 22211420.9, Issued on May 10, 2023, 10 pages.

*Primary Examiner* — Jack Dinh

(74) *Attorney, Agent, or Firm* — Faegre Drinker Biddle & Reath LLP

(57)　　　　ABSTRACT

A movement mechanism (110) for an ophthalmic imaging apparatus (100) for imaging an eye (120) using light propagating along a first optical path and a second optical path, the movement mechanism arranged to move a first optical element into and out of the first optical path, and concurrently move a second optical element into and out of the second optical path, the movement mechanism arranged to rotate the optical elements between a first rotational position and a second rotational position such that the first and second optical element are: in the first and second optical path, respectively, when the optical elements are at the first rotational position and the imaging apparatus is operating in a first imaging mode; and out of the first and second optical path, respectively, when the optical elements are at the second rotational position and the imaging apparatus is operating in a second imaging mode.

14 Claims, 8 Drawing Sheets

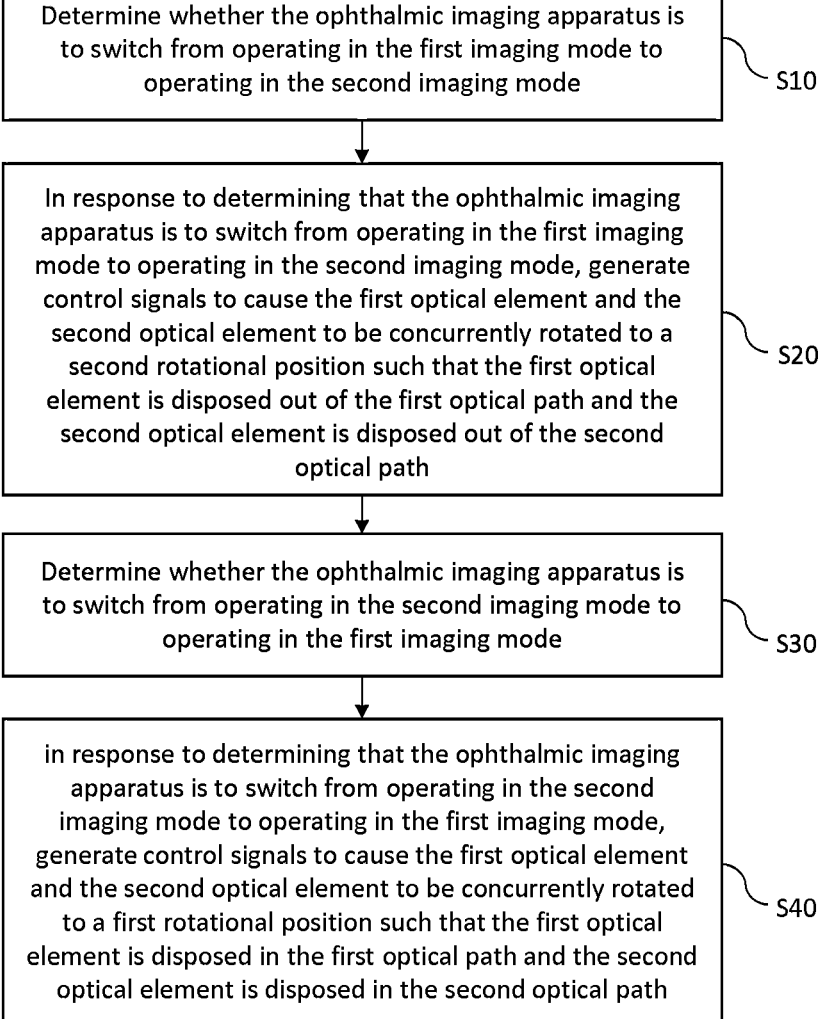

Determine whether the ophthalmic imaging apparatus is to switch from operating in the first imaging mode to operating in the second imaging mode — S10

In response to determining that the ophthalmic imaging apparatus is to switch from operating in the first imaging mode to operating in the second imaging mode, generate control signals to cause the first optical element and the second optical element to be concurrently rotated to a second rotational position such that the first optical element is disposed out of the first optical path and the second optical element is disposed out of the second optical path — S20

Determine whether the ophthalmic imaging apparatus is to switch from operating in the second imaging mode to operating in the first imaging mode — S30 in response to determining that the ophthalmic imaging apparatus is to switch from operating in the second imaging mode to operating in the first imaging mode, generate control signals to cause the first optical element and the second optical element to be concurrently rotated to a first rotational position such that the first optical element is disposed in the first optical path and the second optical element is disposed in the second optical path — S40

Fig. 7

OPTICAL ELEMENT MOVEMENT MECHANISM FOR MULTI-MODALITY OPHTHALMIC IMAGING SYSTEMS

FIELD

Example aspects herein generally relate to the field of ophthalmic imaging systems and, in particular, to mechanisms for moving optical elements into and out of optical paths in multi-modality ophthalmic imaging systems.

BACKGROUND

Some ophthalmic imaging systems are capable of imaging the eye using more than one imaging modality, to acquire different types of images that provide complementary information which is helpful for diagnosing a variety of ocular diseases. For example, a multi-modal ophthalmic imaging apparatus may take the form of an instrument for fundus photography, such as a confocal scanning laser ophthalmoscope (SLO), which is configured to acquire images (in some cases, widefield or ultra-widefield (UWF) images) of the ocular fundus using two or more of the following imaging modalities: full-colour (the appearance of drusen therein being considered pathognomonic of age-related macular degeneration), red-free (useful for observing retinal blood vessels and associated haemorrhages, pale lesions such as drusen and exudates, and nerve fibre layer (NFL) defects), autofluorescence (which allows visualisation of metabolic changes at the level of the retinal pigment epithelium (RPE) and helps to identify areas at risk of developing geographic atrophy or choroidal neovascularisation), and angiography (for imaging the eye's vascular networks), for example Fluorescein angiography (FA) or Indocyanine green (ICG) angiography. By way of an example, the Optos™ California™ system is an UWF SLO having all of the aforementioned imaging modalities. It is also known to combine one or more of the aforementioned imaging modalities with optical coherence tomography (OCT) as a further imaging modality, as in the Optos™ Silverstone™ system, for example.

However, the provision of several imaging modalities in a single ophthalmic imaging apparatus tends to increase the size and complexity of the apparatus, even though the available imaging modalities typically share one or more components of the ophthalmic imaging apparatus, such as the laser source and/or the scanning system. One or more optical elements, which are specific to a particular modality, tend to be moved into the optical path when that modality is to be used, and are moved out of the optical path when another imaging modality is to be used that does not require (or would be adversely affected by) the optical element(s). By way of an example, in a multi-modality ophthalmic imaging apparatus in the form of a multi-modal SLO having full-colour reflectance and autofluorescence (AF) imaging modalities, the light source, beam scanning system and photodetectors are typically used in both imaging modalities. In the full-colour mode, a polariser and a quarter-wave plate are often required in the return optical path to improve image quality. However, these optical elements would decrease signal-to-noise if used in the AF mode, as they would attenuate the much lower intensity return light signal that is typically encountered in this imaging mode, and are therefore usually removed from the return optical path for AF imaging.

In a conventional ophthalmic imaging apparatus, the optical element(s) required for a specific imaging mode is/are usually translated into and out of the return optical path by a mechanical movement mechanism that provides the required translation. Continuing the above multi-modal SLO example, the polariser and the quarter wave plate are usually mounted on a supporting frame, which slides these components into the return optical path for imaging in the full-colour mode, and slides them out of the return optical path for imaging in the AF mode. Conventionally, this translational movement is usually achieved using a mechanism for converting the rotation of a motor to the required translational motion, such as a rack and pinion, a screw (e.g. ball screw or lead screw) actuator or a crank, for example.

However, these conventional (translational) movement mechanisms tend to occupy a significant volume within the ophthalmic imaging apparatus, which is not desirable given typical spatial constraints. Further, these movement mechanisms may (depending on the optical arrangement in the imaging system) be required to lift the optical element(s) against gravity, which increases the torque requirements of the motor and may, in some cases, induce slippage within the rotation-translation conversion mechanism. These rotation-translation conversion mechanism also tend to be slow in moving the optical element(s) into and out of the optical return path, which can limit how quickly the ophthalmic imaging system can switch from one imaging modality to another.

SUMMARY

There is provided, in accordance with a first example aspect herein, a movement mechanism for use in an ophthalmic imaging apparatus which is operable in a first imaging mode and a second imaging mode to acquire images of a portion of an eye. The ophthalmic imaging apparatus comprises a light source, a photodetector, and an optical system. The optical system is arranged to illuminate the portion of the eye with light from the light source and collect light from the illuminated portion of the eye, the optical system being further arranged to split the collected light into a first light and a second light, and guide the first light towards the photodetector via a first optical path passing through the movement mechanism, and the second light to the photodetector via a second optical path passing through the movement mechanism, the first optical path being different from the second optical path. The movement mechanism is arranged to move a first optical element into and out of the first optical path, and concurrently move a second optical element into and out of the second optical path. The movement mechanism comprises an optical element mount arranged to support the first optical element and the second optical element, the optical element mount being operable to rotate each of the first optical element and the second optical element between a first rotational position and a second rotational position such that: the first optical element is disposed in the first optical path and the second optical element is disposed in the second optical path when the first optical element and the second optical element are in the first rotational position; and the first optical element is disposed out of the first optical path and the second optical element is disposed out of the second optical path when the first optical element and the second optical element are at the second rotational position. The movement mechanism further comprises an actuator arranged to drive the optical element mount so as to set the first optical element and the second optical element to the first rotational position or the second rotational position. The movement mechanism further comprises a controller arranged to control the actuator to set the rotational position of the first optical element and the second optical element to the first rotational position when the ophthalmic imaging apparatus is operating in the first imaging mode, and the second rotational position when the ophthalmic imaging apparatus is operating in the second imaging mode.

In a first example embodiment of the movement mechanism of the first example aspect, the optical element mount comprises a first rotatable mount arranged to support the first optical element, the first rotatable mount being rotatable, about a first rotational axis, such that, when at the first rotational position, the first optical element is disposed in the first optical path and, when at the second rotational position, the first optical element is disposed out of the first optical path. In the first example embodiment, the optical element mount further comprises a second rotatable mount arranged to support the second optical element, the second rotatable mount being rotatable, about a second rotational axis, such that, when at the first rotational position, the second optical element is disposed in the second optical path and, when at the second rotational position, the second optical element is disposed out of the second optical path, wherein the first rotational axis is parallel to the second rotational axis, the first rotational axis is perpendicular to the first optical path, and the second rotational axis is perpendicular to the second optical path. In the first example embodiment, the movement mechanism further comprises a mechanical link between first rotatable mount and the second rotatable mount, the mechanical link being arranged to cause concurrent rotation of one of the first rotatable mount and the second rotatable mount when the other of the first rotatable mount and the second rotatable mount is rotated. In the first example embodiment, the actuator is arranged to rotate one of the first rotatable mount and the second rotatable mount about the respective one of the first rotational axis and the second rotational axis, and the controller is arranged to control the actuator to rotate the one of the first rotatable mount and the second rotatable mount such that, when at the first rotational position, the first optical element is disposed in the first optical path and the second optical element is disposed in the second optical path and, when at the second rotational position, the first optical element is disposed out of the first optical path and the second optical element is disposed out of the second optical path. In the first example embodiment, the first rotational axis and the second rotational axis may pass through the first optical path and the second optical path, respectively.

In a second example embodiment of the movement mechanism of the first example aspect, the optical element mount comprises a rotatable mount arranged to support the first optical element and the second optical element, the rotatable mount being rotatable, about a rotational axis perpendicular to the first optical path and the second optical path, such that: when at the first rotational position, the first optical element is disposed in the first optical path and, when at the second rotational position, the first optical element is disposed out of the first optical path; and when in the first rotational position, the second optical element is disposed in the second optical path and, when at the second rotational position, the second optical element is disposed out of the second optical path. In the second example embodiment, the actuator is arranged to rotate the rotatable mount about the rotational axis, and the controller is arranged to control the actuator to rotate the rotatable mount such that, when at the first rotational position, the first optical element is disposed in the first optical path and the second optical element is disposed in the second optical path and, when at the second rotational position, the first optical element is disposed out of the first optical path and the second optical element is disposed out of the second optical path.

In the first and/or second example embodiment set out above, the movement mechanism may be further arranged to, when moving the first optical element into and out of the first optical path and concurrently moving the second optical element into and out of the second optical path, concurrently move a third optical element into and out of the first optical path, by the optical element mount being further arranged to support the third optical element and rotate the third optical element such that the third optical element is disposed in the first optical path when the first optical element and the second optical element are at the first rotational position, and such that the third optical element is disposed out of the first optical path when the first optical element and the second optical element are at the second rotational position.

Where the first example embodiment includes the above arrangement of the movement mechanism: the first rotatable mount may comprise a hollow cuboid arranged to support the first optical element on a first side of the cuboid, and arranged to support the third optical element on an opposing second side of the cuboid; each of the first side of the cuboid and the second side of the cuboid has a respective opening to allow light to propagate along the first optical path, through the cuboid and the first and third optical elements, when the first optical element and the second optical element are at the first rotational position; and each of a third side of the cuboid and an opposing fourth side of the cuboid has a respective opening to allow light to propagate along the first optical path, through the cuboid and without passing through any optical element, when the first optical element and the second optical element are at the second rotational position. In this case, the movement mechanism may further comprise the first optical element and the third optical element, wherein the first optical element comprises a polariser, and the third optical element comprises a wave plate.

Additionally or alternatively, where the first example embodiment includes the above arrangement of the movement mechanism, the optical element mount may further comprise the first optical element and the third optical element, the optical element mount being operable to rotate the first optical element and the third optical element about a rotational axis which is inclined with respect to a direction of a force of gravity acting on the optical element mount, the first optical element and the third optical element having different respective moments about the rotational axis, wherein the movement mechanism further comprises a counter-balance arranged to reduce a resultant moment about the rotational axis, the resultant moment comprising a combination of the moment of the first optical element about the rotational axis and the moment of the third optical element about the rotational axis. In this case, the third optical element may be rotatably mounted on the optical element mount so as to be manually rotatable about the optical element mount.

In the first example aspect or any of its embodiments set out above, the first optical element and/or the second optical element may, in accordance with a further example embodiment, be rotatably mounted on the optical element mount so as to be manually rotatable about the optical element mount.

In the first example aspect or any of its embodiments set out above, the optical element mount comprise a protruding part arranged to rotate with rotation of the first optical element and the second optical element so as to move along an arc of a circle, and the movement mechanism may further comprise: an optical detector arranged to detect the protruding part when the protruding part is rotated into a vicinity of the optical detector during rotation of the first optical element and the second optical element, the optical detector being disposed in the movement mechanism such that a detection of the protruding part by the optical detector indicates that the first optical element and the second optical element are at one of the first rotational position and the second rotational position; and a housing for the optical detector, the housing being arranged to surround the optical detector so as to suppress an egress of light from the optical detector to an exterior of the housing. In this case, the optical detector may be a first optical detector, and the movement mechanism may further comprise a second optical detector arranged to detect the protruding part when the protruding part is rotated into a vicinity of the second optical detector during rotation of the first optical element and the second optical element, the second optical detector being disposed in the movement mechanism such that a detection of the protruding part by the second optical detector indicates that the first optical element and the second optical element are at the other of the first rotational position and the second rotational position. Furthermore, the housing may be further arranged to surround the second optical detector so as to suppress an egress of light from the second optical detector to the exterior of the housing, the housing being further arranged to suppress propagation of light between the first optical detector and the second optical detector. The optical detector may be attached to the housing, and the housing may be detachable from the movement mechanism.

There is provided, in accordance with a second example aspect herein, an ophthalmic imaging apparatus operable in a first imaging mode and a second imaging mode to acquire images of an eye. The ophthalmic imaging apparatus comprises a light source, a photodetector, and an optical system arranged to illuminate a portion of an eye with light from the light source and collect light from the illuminated portion of the eye, the optical system being further arranged to split the collected light into a first light and a second light, and guide the first light towards the photodetector via a first optical path, and the second light to the photodetector via a second optical path, the first optical path being different from the second optical path. The ophthalmic imaging apparatus further comprises a movement mechanism according to the first example aspect or any of its embodiments set out above, the movement mechanism being arranged to move a first optical element into and out of the first optical path, and concurrently move a second optical element into and out of the second optical path, wherein the first optical path and the second optical path pass through the movement mechanism. The first imaging mode may be a reflectance imaging mode, wherein the ophthalmic imaging apparatus acquires a reflectance image of the eye, the second imaging mode may be a fluorescence imaging mode, wherein the ophthalmic imaging apparatus acquires a fluorescence image of the eye, and each of the first optical element and the second optical element may comprise a polariser.

There is further provided, in accordance with a third example aspect herein, a computer-implemented method of controlling movement of optical elements into and out of respective optical paths in an ophthalmic imaging apparatus which is operable in a first imaging mode and a second imaging mode to acquire images of a portion of an eye. The ophthalmic imaging apparatus comprises: a light source; a photodetector; and an optical system arranged to illuminate the portion of the eye with light from the light source and collect light from the illuminated portion of the eye, the optical system being further arranged to split the collected light into a first light and a second light, and guide the first light towards the photodetector via a first optical path, and the second light to the photodetector via a second optical path, the first optical path being different from the second optical path. The method comprises: determining whether the ophthalmic imaging apparatus is to switch from operating in the first imaging mode to operating in the second imaging mode; in response to determining that the ophthalmic imaging apparatus is to switch from operating in the first imaging mode to operating in the second imaging mode, generating control signals to cause the first optical element and the second optical element to be concurrently rotated to a second rotational position such that the first optical element is disposed out of the first optical path and the second optical element is disposed out of the second optical path; determining whether the ophthalmic imaging apparatus is to switch from operating in the second imaging mode to operating in the first imaging mode; and in response to determining that the ophthalmic imaging apparatus is to switch from operating in the second imaging mode to operating in the first imaging mode, generating control signals to cause the first optical element and the second optical element to be concurrently rotated to a first rotational position such that the first optical element is disposed in the first optical path and the second optical element is disposed in the second optical path.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 7 is a flow diagram illustrating a computer-implemented method of controlling movement of optical elements according to a second example embodiment herein.

DETAILED DESCRIPTION OF EXAMPLE EMBODIMENTS

In view of the need for a movement mechanism which at least partly addresses the above-described issues with conventional translational movement mechanisms, the present inventors have devised a movement mechanism which is arranged to move a first optical element and a second optical element into and out of a first optical path and a second optical path, respectively, by rotation of the optical elements. By rotating the optical elements rather than translating them, readily available rotational actuators, such as electric motors, can be used whilst avoiding the need for a rotation-translation conversion mechanism and the associated shortcomings, such as slippage and delay in moving the optical elements into and out of the return optical paths. In addition, the devised movement mechanism allows for the option of the motor directly rotating one or more of the optical elements into and out of an optical path, thus removing the need for gearing. This may reduce the movement mechanism's weight and component count.

Further, rotating optical elements rather than sliding them into and out of an optical path may allow the optical elements to be stored, when out of the return optical path, closer to a side of the return optical path, which may help reduce the size of the movement mechanism.

In addition, in some example embodiments, where the movement mechanism is arranged to move one or more optical elements against gravity, the movement of the optical component(s) into and out of the optical path by rotation about a rotational axis may also pave the way for the required torque to be reduced, by distributing the driven mass around the rotational axis or by orienting the rotational axis so that the actuator of the movement mechanism is not required to counter a torque caused by gravity.

Example embodiments herein will now be described in detail with reference to accompanying drawings.

Figure 1:
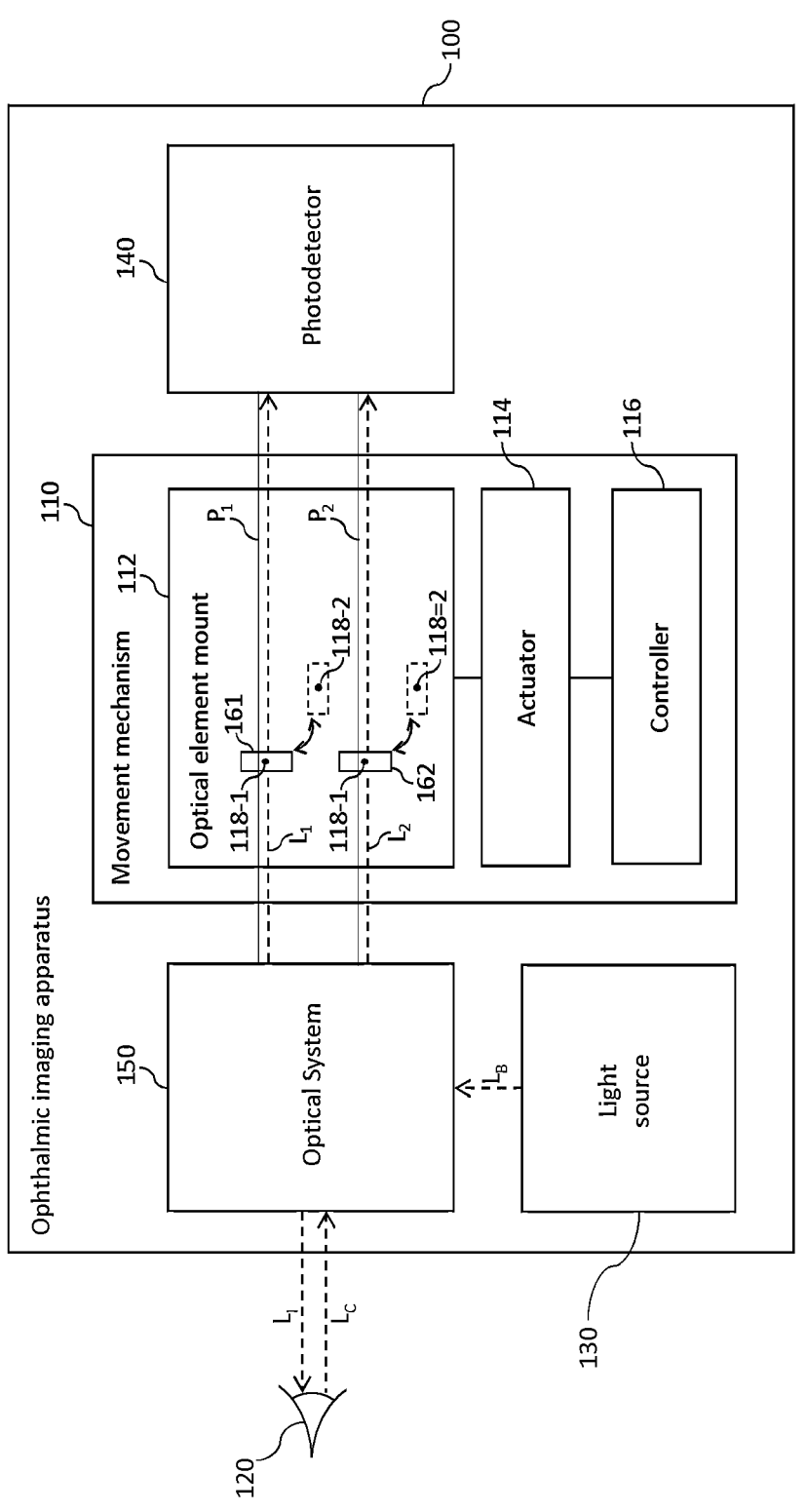
FIG. 1 is a schematic illustration of an ophthalmic imaging apparatus comprising a movement mechanism according to an example embodiment herein.

FIG. 1 is a schematic illustration of an ophthalmic imaging apparatus 100, which comprises a movement mechanism 110 according to a first example embodiment. The movement mechanism 110 may, as in the present example embodiment, be detachably mounted in the ophthalmic imaging apparatus 100 so that it can be removed for inspection and adjustment, for example, and then re-installed, as necessary. The ophthalmic imaging apparatus 100 is operable to image an eye 120 in a first imaging mode and a second imaging mode, and comprises, in addition to the movement mechanism 110, a light source 130, a photodetector 140, and an optical system 150.

The optical system 150 is arranged to illuminate the portion of the eye 120 with light, $L_I$, from the light source 130 and collect light, $L_C$, from the illuminated portion of the eye 120. The illuminated portion of the eye 120 may, as in the present example embodiment, comprise a portion of the retina of the eye 120, although the illuminated portion is not so limited and may alternatively comprise another part of the eye 120, such as a portion of the anterior segment, for example. The optical system 150 is further arranged to split the collected light $L_C$ into a first light, $L_1$, and a second light, $L_2$, which may, as in the present example embodiment, have different spectral content, with the first light $L_1$ having a first wavelength, $\lambda_1$ (or a (narrow) range of wavelengths centred on $\lambda_1$), and the second light $L_2$ having a second wavelength, $\lambda_2$ (or a (narrow) range of wavelengths centred on $\lambda_2$, which does not overlap the range of wavelengths centred on $\lambda_2$). The optical system 150 may, as in the present example embodiment, comprise a first dichroic filter for splitting off the first light $L_1$ from the collected light $L_C$, and a second dichroic filter for splitting off the second light $L_2$ from the collected light $L_C$.

The optical system 150 is further arranged to convey or guide (using one or more optical components, such as optical fibres, mirrors and the like) the first light $L_1$ towards the photodetector 140 via an optical path that includes a first (linear) optical path, $P_1$, which passes through the movement mechanism 110 when the movement mechanism 110 is installed in the ophthalmic imaging apparatus 100, and convey or guide the second light $L_2$ to the photodetector 140 via an optical path that includes a second, different (linear) optical path, $P_2$, which also passes through the movement mechanism 110 when the movement mechanism 110 is installed in the ophthalmic imaging apparatus 100. The second optical path $P_2$ may, as in the present example embodiment, be parallel to the first optical path $P_1$. It should be noted, however, that the number of components into which the collected light $L_C$ is split by the optical system 150 is not limited to two, and that more than two such components may be conveyed or guided towards the photodetector 140 via respective optical paths passing through the movement mechanism 110. The teachings herein relating to the components of the ophthalmic imaging apparatus 100 that provide sources for and affect light propagating along the first optical path $P_1$ and the second optical path $P_2$ are applicable to additional such components that may be included to provide source(s) for and affect light propagating along one or more addition optical paths passing through the movement mechanism 110.

The light source 130 is, in general, arranged to generate light in one or more ranges of wavelength that are suitable for imaging the eye 120, for example in the visible spectrum (e.g. red and green light) and/or the near-infrared spectrum. The light source 110 may, for example, comprise one or more laser diodes or super-luminescent diodes (or a combination of laser diodes or super-luminescent diodes), and may also have one or more optical components (such as collimators, apertures, lens) arranged to generate one or more light beams. By way of an example, the light source 130 of the present example embodiment comprises a red laser arranged to generate red light (e.g. of 635 nm wavelength), and a green laser arranged to generate green light (e.g. of 532 nm wavelength), although it will be appreciated that the light source 130 may more generally comprise a first laser arranged to generate light of a first wavelength (defining a first optical channel of the ophthalmic imaging apparatus 100) and a second laser arranged to generate light of a second, different wavelength (defining a second optical channel of the ophthalmic imaging apparatus 100). The two optical channels may, as in the present example embodiment, be combined in a single beam of the light $L_1$ with which the portion of the eye 120 is illuminated by the optical system 150. However, the optical system 150 may alternatively illuminate the portion of the eye 120 with two separate beams, each containing a respective one of the optical channels. In either case, the optical system (discussed further below) may be arranged to illuminate the portion of the eye 120 with a (flying) spot of light or a line of light (in case of the ophthalmic imaging apparatus 100 being a line-field system) generated using a cylindrical lens or other well-known components or optical assemblies for generating line-field illumination.

In example embodiments wherein the ophthalmic imaging apparatus 100 is operable in an OCT imaging mode, the light source 130 may further comprise a swept light source (in case of the ophthalmic imaging apparatus 100 being a swept-source OCT (SS-OCT) system) or a broadband source (in case of the ophthalmic imaging apparatus 100 being a spectral-domain OCT (SD-OCT) system).

The photodetector 140 may, as in the present example embodiment, comprise a first photodetector (not shown), which is arranged to detect the first light $L_1$, and a second detector (not shown), which is arranged to detect the second light $L_2$. However, the photodetector 120 may instead comprise a single photodetector arranged to detect both the first light $L_1$ and second light $L_2$. The photodetector 140 may comprise one or more balanced photodetector arrangements (each comprising two reverse-biased photodiodes whose output photocurrents are subtracted from one another, the subtracted current signal being converted to a voltage detection signal by a transimpedance amplifier). In example embodiments where the ophthalmic imaging apparatus 100 features an OCT imaging modality, the photodetector 140 may further comprise a spectrometer (where a SD-OCT set-up is used) or a photodiode detector (where a SS-OCT set-up is used).

Figure 2:
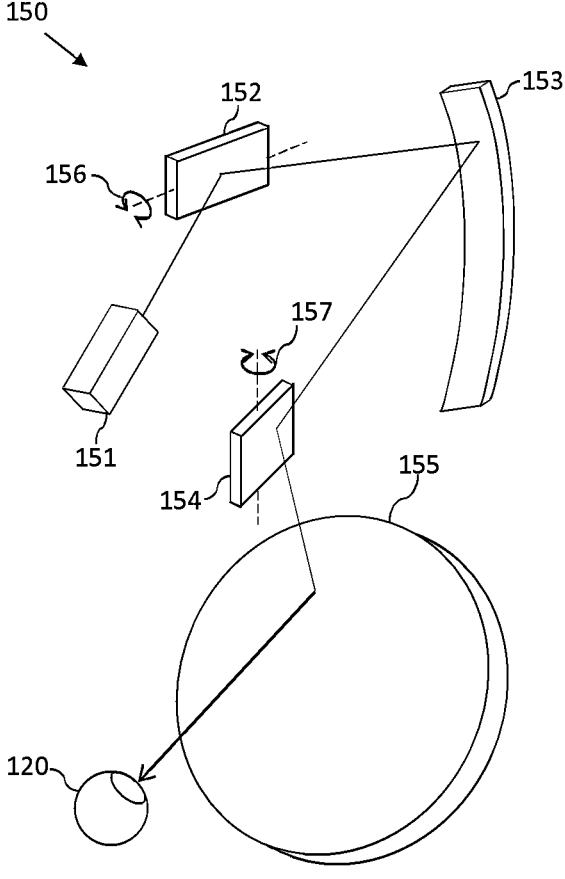
FIG. 2 is a schematic illustration of an example of a scanning system forming part of the ophthalmic imaging apparatus.

The optical system 150 may, as in the present example embodiment, comprise a scanning system, which is arranged to perform a two-dimensional point-scan of the light $L_1$ from the light source 130 light across a portion of the eye 120 that is illuminated by the point-scan, and to collect light from the illuminated region during the point-scan. An example of such an optical system is illustrated in FIG. 2. The optical system 150 may, as in the present example embodiment, comprise a scanning element and a mirror, wherein the optical system 150 is arranged to perform the two-dimensional point scan by the scanning element scanning a light beam across the portion of the eye 120 via the mirror. An example of such a scanning system, which can perform a wide-field retinal scan, is described in WO 2014/53824 A1, the content of which is incorporated herein by reference in its entirety. Components of such a scanning system are shown in FIG. 2 and comprise an optical coupler 151, a first scanning element 152, a first curved mirror 153, a second scanning element 154 and a second curved mirror 155. The light beam enters the optical system 150 via the optical coupler 151. The light beam is then reflected, in sequence, by the first scanning element 152, the first curved mirror 153, the second scanning element 154 and the second curved mirror 155, before being incident on the eye 120. Light from the illuminated portion of the eye 120 collected by the optical system 150 follows the same optical path through the optical system 150 as the light beam that had entered the optical system 150 via the optical coupler 151 but in reverse order, and exits the optical system 150 via the optical coupler 151.

The two-dimensional point scan is performed by the first scanning element 152 rotating around a first axis 156 to scan the light beam in a first direction across the portion of the eye 120, and by the second scanning element 154 rotating around a second axis 157 to scan the light beam in a second direction across the portion of the eye 120 (which may, as in the present example embodiment, be orthogonal to the first direction). Thus, by rotating the first scanning element 152 and the second scanning element 154, it is possible to steer the light beam to different locations on the portion of the eye 120. The rotation of the first scanning element 152 and the second scanning element 154 may be coordinated by a scanning system controller (not shown) such that the light beam is scanned across the portion of the eye 120 in accordance with a predefined scan pattern.

In the example of FIG. 2, the first curved mirror 153 is an ellipsoidal mirror (and referred to as a slit mirror), and the second curved mirror 155 is also an ellipsoidal mirror. Each of the ellipsoidal mirrors has a respective first focal point and a respective second focal point. The first scanning element 152 is disposed at the first focal point of the first curved mirror 153, and the second scanning element 154 is disposed at the second focal point of the first curved mirror 153. The second scanning element 154 is also disposed at the first focal point of the second curved mirror 155, and the eye 120 (more specifically, the pupil of the eye 130 in the present example) is disposed at the second focal point of the second curved mirror 155.

The first scanning element 152 and the second scanning element 154 may, as in the present example embodiment, each be a galvanometer optical scanner (or "galvo"), although another type of scanning element could alternatively be used, such as a MEMS scanning mirror or a resonant scanning mirror, for example.

An optical system 150 of the kind described above with reference to FIG. 2 may be used in a variety of imaging modes, such as colour, red-free, AF, ICG and OCT (among others). However, the optical system 150 may alternatively be arranged in other ways, for example to instead perform a line-field scan across the imaged portion of the eye 120. The optical system 150 may further comprise additional optical components, such as optical components for filtering, guiding and/or collimating the light $L_B$ from the light source 130, and a cylindrical lens or other means of generating a line of light in case the optical system 150 is a line-field system.

Referring again to FIG. 1, the movement mechanism 110 comprises an optical element mount 112, an actuator 114 and a controller 116. The movement mechanism 110 is arranged to move a first optical element 161 into and out of the first optical path $P_1$ (without the first optical element 161 ever entering the second optical path $P_2$) and concurrently move a second optical element 162 into and out of the second optical path $P_2$ (without the second optical element 162 ever entering the first optical path $P_1$). Further, the movement mechanism 110 may, as in the present example embodiment, be arranged to, when moving the first optical element 161 into and out of the first optical path $P_1$ and concurrently moving the second optical element 162 into and out of the second optical path $P_2$, concurrently move a third optical element (not shown in FIG. 1) into and out of the first optical path $P_1$ and/or concurrently move a fourth optical element (not shown in FIG. 1) into and out of the second optical path $P_2$.

The movement mechanism 110 may be arranged to, when moving the first optical element 161 into and out of the first optical path $P_1$ and concurrently moving the second optical element 162 into and out of the second optical path $P_2$, concurrently move a fifth optical element (not shown in FIG. 1), such as a filter (e.g. an infrared filter), into and out of the first optical path $P_1$ or the second optical path $P_2$, such that the fifth optical element is disposed in one of the first optical path $P_1$ and the second optical path $P_2$ when the first optical element 161 and the second optical element 162 are at the second rotational position 118-2 described below, and such that the fifth optical element is disposed out of the one of the first optical path $P_1$ and the second optical path $P_2$ when the first optical element 161 and the second optical element 162 are at the first rotational position 118-1 described below.

Figure 3B:
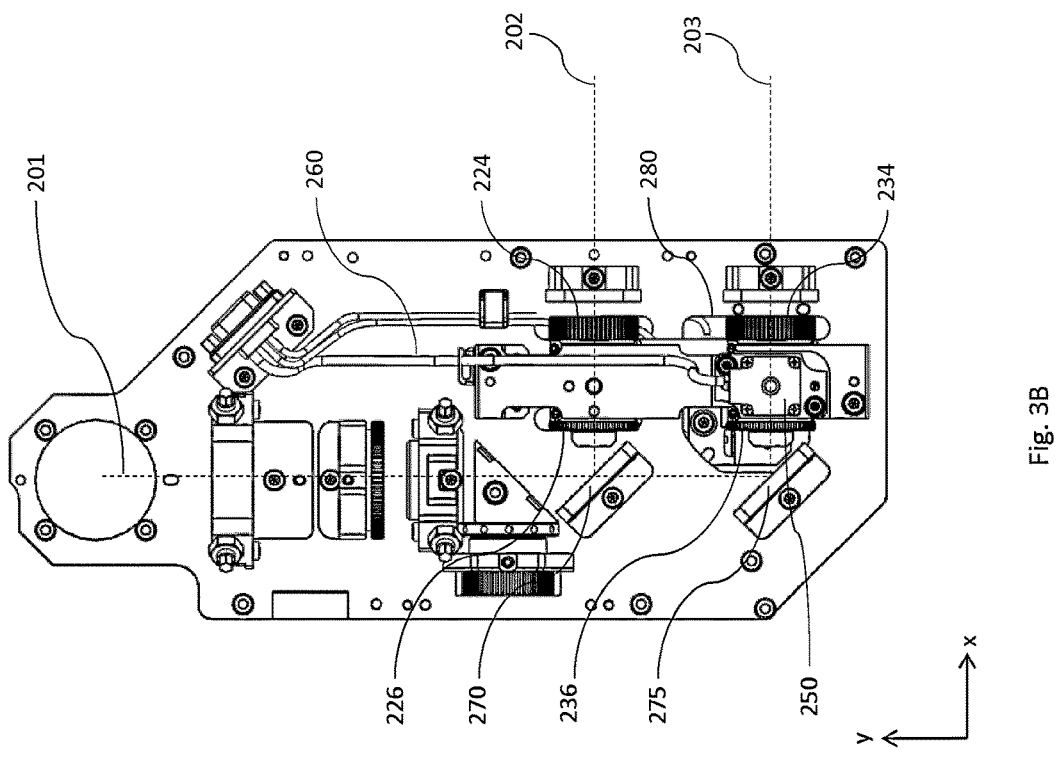
FIG. 3B is a top view of the module shown in FIG. 3A.
Figure 3A:
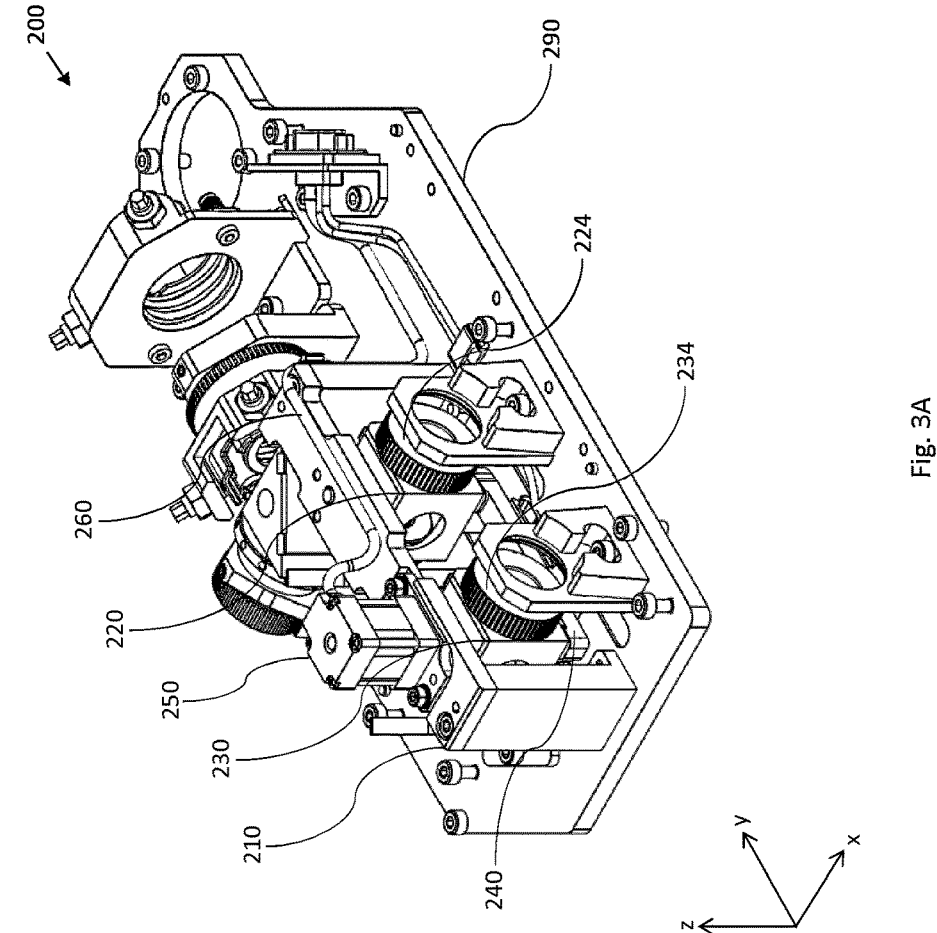
FIG. 3A is an isometric view of a module comprising a movement mechanism according to the example embodiment herein and components of an optical system 130, wherein the optical elements in the movement mechanism are at a first rotational position so to be disposed in respective optical paths.

FIGS. 3A and 3B are an isometric view and a top view, respectively, of a module 200 of the ophthalmic imaging apparatus 100, which module comprises a movement mechanism, an optical element mount 210, a first optical path 202, a second optical path 203, a first optical element 224, a second optical element 234, a third optical element 226, a fourth optical element 236, and components of an optical system that form examples or example implementations (as the case may be) of the movement mechanism 110, the optical element mount 112, the first optical path $P_1$, the second optical path $P_2$, the first optical element 161, the second optical element 162, the third optical element, the fourth optical element, and components of the optical system 150, respectively, that have been described above with reference to FIG. 1. In the present example embodiment, the actuator 114 is provided in the form of an electric motor 250.

The illustrated components of the module 200 are secured to a base plate 290 of the module 200, although these components may alternatively be provided in the illustrated arrangement on one or more other parts of the ophthalmic imaging apparatus 100.

During operation of the ophthalmic imaging apparatus 100, the collected light $I_C$ may, as in the present example embodiment, enter the module 200 along an entry optical axis 201 (parallel to a y-axis direction) and pass through any components of the optical system 130 (unlabelled), such as a dichroic, that may be provided to split off blue light. The collected light $I_C$ may, as in the present example embodiment, be split into the first light $L_1$ and the second light $L_2$ mentioned above using two dichroic mirrors. More specifically, during imaging by the ophthalmic imaging apparatus 100, the collected light $I_C$ is incident on a first dichroic 270, which is arranged to split off the first light $L_1$ from the collected light $I_C$ by reflecting light of the first wavelength $\lambda_1$ along the first (linear) optical path 202 (parallel to the x-axis) towards the photodetector 140 (not shown in FIGS. 3A and 3B). The portion of the collected light $I_C$ that has not been split off by the first dichroic 270 is incident on a second dichroic 275, which is arranged to split off the second light $L_2$ from the collected light $I_C$ by reflecting light of the second wavelength $\lambda_2$ along the second (linear) optical path 203 (also parallel to the x-axis) towards the photodetector 140. However, the components of the optical system 150 which guide the first light $L_1$ and the second light $L_2$ to the first optical path 202 and the second optical path 203, respectively, are not so limited. For example, the second dichroic 275 may be replaced by a conventional mirror in another example embodiment. The first light $L_1$ and second light $L_2$ may enter the module 200 along any optical path that is determined by the optical arrangement used in the optical system 150.

The optical element mount 210 is arranged to support both the first optical element 224 and the second optical element 234. The optical element mount 210 may, as in the present example embodiment, be further arranged to support the third optical element 226 and the fourth optical element 236, and may also be modified to support the fifth optical element. By way of an example, the optical element mount 210 may, as in the present example embodiment, comprise a first rotatable mount 220 arranged to support the first optical element 224 and the third optical element 226, and a second rotatable mount 230, which is arranged to support the second optical element 234 and the fourth optical element 236, as well as the fifth optical element (where provided). It is noted that the fifth optical element (where provided) may alternatively be mounted on the first rotatable mount 220.

It is also noted that the optical element mount 210 need not have two separate rotatable mounts, as set out above, but may, as described in more detail below, alternatively comprise a single rotatable mount, which is arranged to support the first optical element 224 and the second optical element 234, as well as the third optical element 226, the fourth optical element 236, and the fifth optical element (if included).

The optical element mount 210 may also comprise a bracket, as illustrated in FIG. 3A, which is arranged to support the first rotatable mount 220 and the second rotatable mount 230 so that they can rotate about their respective rotational axes. However, the bracket may be omitted, and the first rotatable mount 220 and the second rotatable mount 230 may alternatively be rotationally mounted solely on the base plate 290.

The first optical element 224 and the second optical element 234 may, as in the present example embodiment, each comprise a polariser. However, either or both these elements may alternatively or additionally comprise another optical element, such as a wave plate, a quarter-wave plate, an optical filter or a lens, for example. The third optical element 226 and the fourth optical element 236 may, as in the present example embodiment, each comprise a wave plate. However, either or both these elements may alternatively or additionally comprise another optical element, such as a polariser, an optical filter or a lens, for example. The above-described fifth optical element, where provided, may comprise an infrared (IR) filter and/or any other optical component, such as a polariser, wave plate or lens, for example. The forms which the aforementioned optical elements take is not limited to the above examples, and will be dictated by the requirements of the imaging modes of the ophthalmic imaging apparatus 100.

When the module 200 is installed in the ophthalmic imaging apparatus 100, the illustrated components of the module 200 are oriented such that the illustrated y-axis direction is vertical (or a few degrees (e.g. less than 15 degrees) from vertical), i.e. is opposite (or nearly so) to the direction of gravity acting on the ophthalmic imaging apparatus 100. Thus, the first rotatable mount 220 is above the second rotatable mount 230 when the movement mechanism is installed in the ophthalmic imaging apparatus 100, with the first optical path 202 and the second optical path 203, and the respective axes of rotation of the first rotatable mount 220 and the second rotatable mount 230, being substantially horizontal.

The first optical element 224 and the second optical element 234 may, as in the present example embodiment, be rotatably mounted on the optical element mount 210 so as to be manually rotatable about the optical element mount 210. Similarly, the third optical element 226, the fourth optical element 236 and the fifth optical element (where provided) may be rotatably mounted on the optical element mount 210 so as to be manually rotatable about the optical element mount 210. However, only some of these optical elements may be rotationally mounted in this way, according to requirements. Thus, in general, any optical element mounted on the first rotatable mount 220 or second rotatable mount 230 may be rotatably mounted so as to be rotatable, by hand, about the optical path passing through the rotatable mount. Where the optical element is a polariser, this manual rotatability allows a technician to rotate the polariser to maximise the elimination of non-retinal signals (including reflections and glare) in the light which returns from the eye, as these artifacts often have a well-defined polarization state as compared to the desired retinal signals.

The first rotatable mount 220 may, as in the present example embodiment, comprise a hollow cuboid arranged to support the first optical element 224 on a first side of the cuboid, and to support the third optical element 226 on an opposing second side of the cuboid. However, the first rotatable mount 220 is not limited to this form, and may take any alternative form that allows it to support the first optical element 224 and the third optical element 226 so that their surfaces, through which the first light $L_1$ passes, are parallel to the axis of rotation of the first rotatable mount 220. Further, the second rotatable mount 230 may, as in the present example embodiment, comprise a second hollow cuboid which shares the same features and alternatives as the hollow cuboid of the first rotatable mount 220. The first hollow cuboid or the second hollow cuboid may also support the fifth optical element noted above.

Figures 4A, 4B:
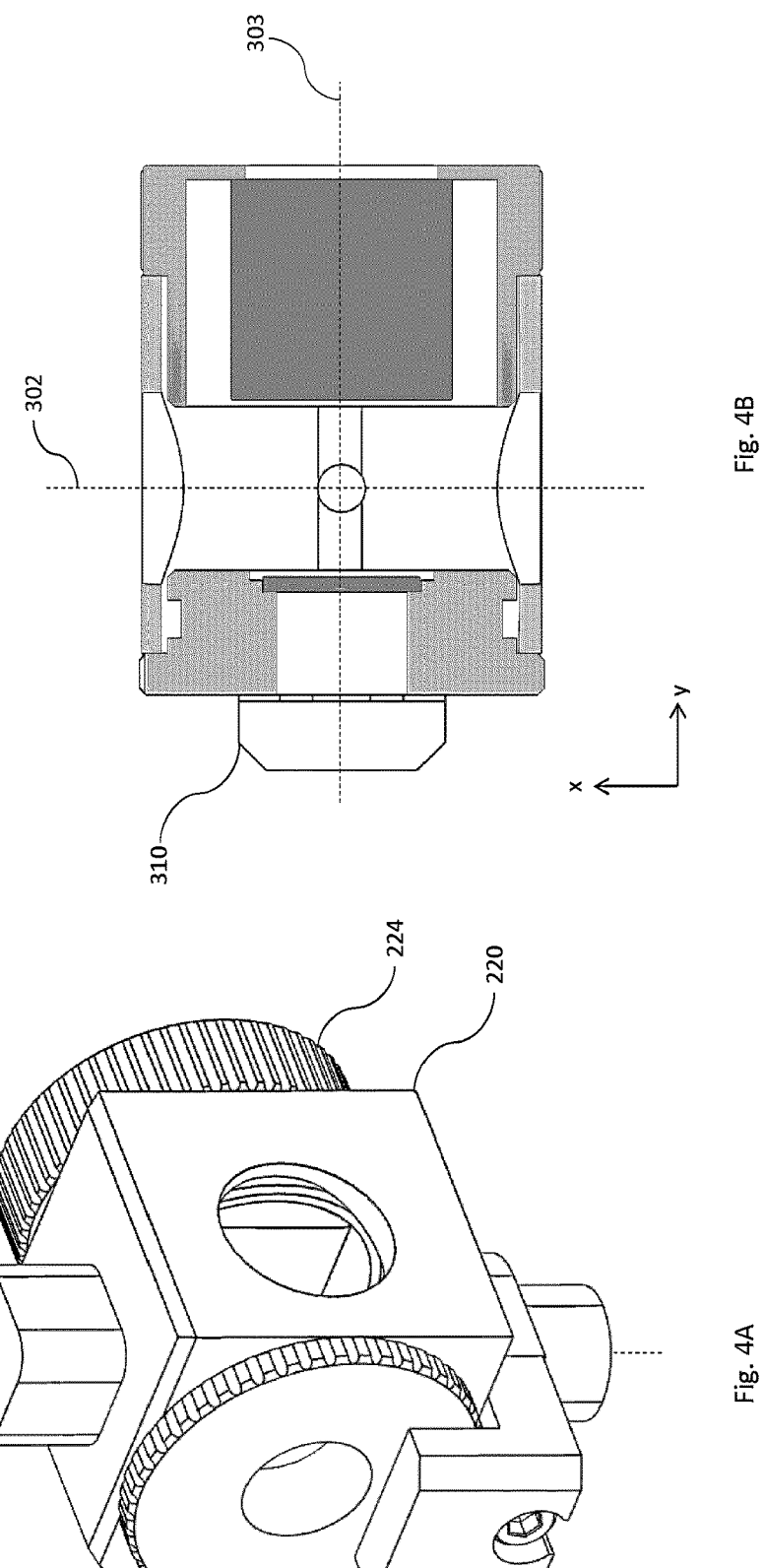
FIG. 4A is an isometric view of the first rotatable mount 220 shown in FIGS. 3A to 3D.
FIG. 4B is a cross-sectional view of the first rotatable mount 220 shown in FIG. 4A.

FIG. 4A is an isometric enlarged view of the first rotatable mount 220 shown in FIGS. 3A and 3B. As previously described, the first rotatable mount 220 of the present example embodiment is a hollow cuboid, having three pairs of parallel opposing sides.

The optical element mount 210 is operable to rotate each of the first optical element 224 and the second optical element 234 between a first rotational position 118-1 and a second rotational position 118-2 such that the first optical element 224 is disposed in the first optical path 202 and the second optical element 234 is disposed in the second optical path 203 when the first optical element 224 and the second optical element 234 are in the first rotational position 118-1. However, when the first optical element 224 and the second optical element 234 are in the second rotational position 118-2, the first optical element 224 is disposed out of the first optical path 202 and the second optical element 234 is disposed out of the second optical path 203, and the first light $L_1$ and the second light $L_2$ are able to propagate along the first optical path 202 and the second optical path 203, respectively, through free space, i.e. without passing through any optical element in the movement mechanism 110. The rotational position of each optical element may be defined in a polar coordinate system (specifically, in terms of an angle of rotation), whose centre is at the axis of rotation of the optical element.

The optical element mount 210 may, as in the present example embodiment, be operable to rotate the third optical element 226 and the fourth optical element 236 such that the third optical element 226 and the fourth optical element 236 are disposed in the first optical path 202 and the second optical path 203, respectively, when the first optical element 224 and the second optical element 234 are at the first rotational position, 118-1, as shown in FIGS. 3A and 3B.

Figure 3D:
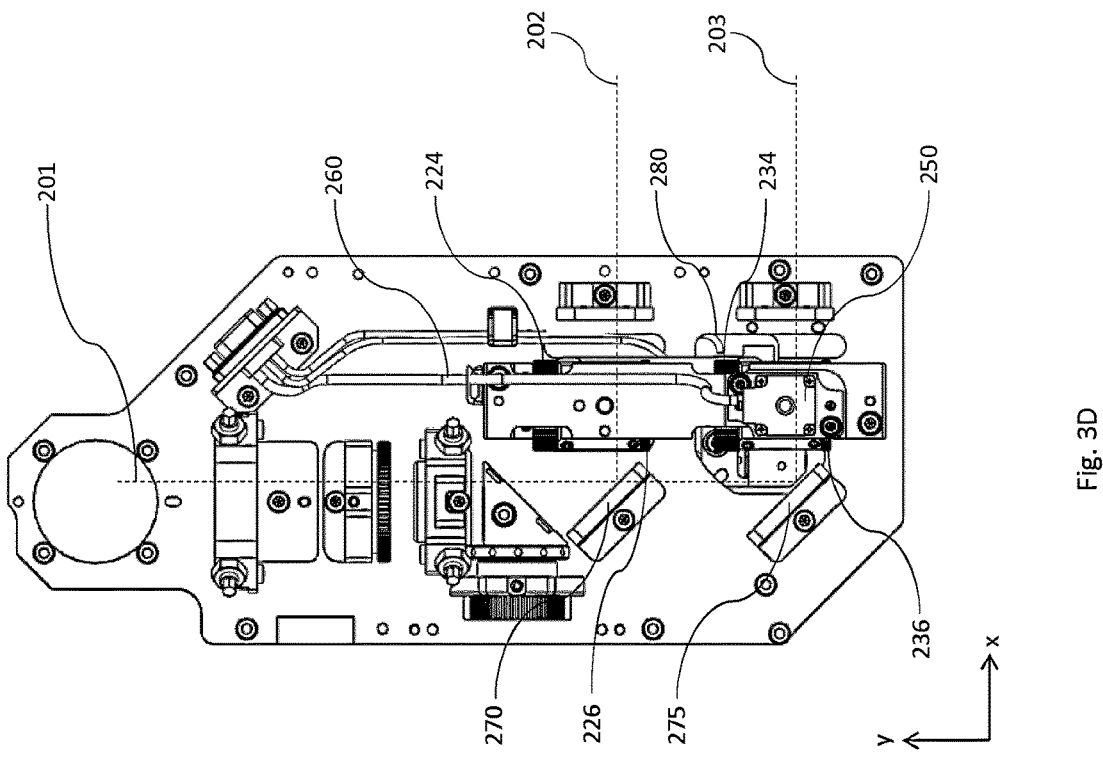
FIG. 3D is a top view of the module shown in FIG. 3C.
Figure 3C:
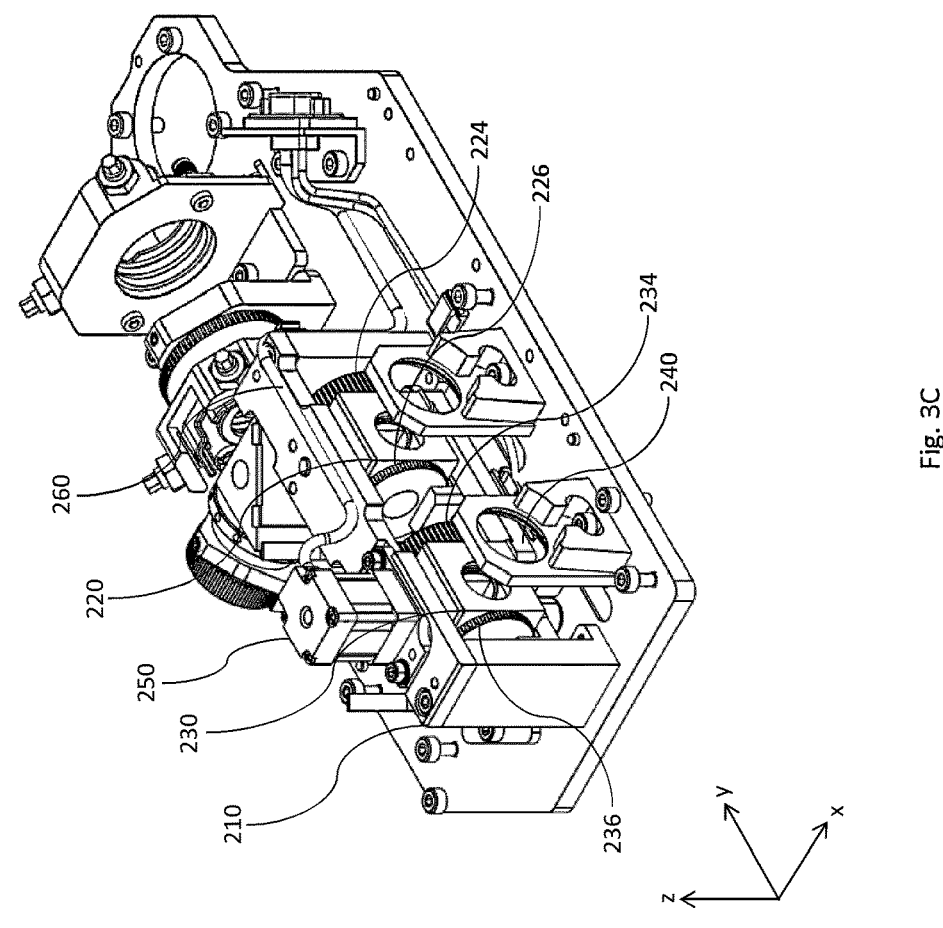
FIG. 3C is an isometric view of the module, wherein the optical elements in the movement mechanism are at a second rotational position so to be disposed out of the respective optical paths.

Further, the optical element mount 210 may, as in the present example embodiment, be operable to rotate the third optical element 226 and the fourth optical element 236 so that they are disposed out of the first optical path 202 and the second optical path 203, respectively, when the first optical element 224 and the second optical element 234 are at the second rotational position 118-2. FIGS. 3C and 3D are an isometric view and a top view, respectively, of the module 200 in a state where the first optical element 224 and the second optical element 234 are at the second rotational position 118-2.

The first rotatable mount 220 may, as in the present example embodiment, be rotatable, about a first rotational axis 301 shown in FIG. 4A, such that, when in the first rotational position 118-1, the first optical element 224 (and the third optical element 226) is disposed in the first optical path 202 and, when in the second rotational position 118-2, the first optical element 224 (and the third optical element 226) is disposed out of the first optical path 202. FIG. 4B is a cross-section view of the first rotatable mount 220, taken through the centre of the hollow cuboid in the x-y plane. The first rotatable mount 220 has a first cuboid axis 302 and a perpendicular second cuboid axis 303. The first rotatable mount 220 is rotatable about the first rotational axis 301 (in the z-axis direction) such that first cuboid axis 302 is aligned with the first optical path 202 (and the x-axis direction) when the first optical element 224 is at the second rotational position 118-2, and the second cuboid axis 303 is aligned with the first optical path 202 when the first optical element 224 is at the first rotational position 118-1. The first rotational axis 301 is perpendicular to the first optical path 202 (and the entry axis 201). However, the first rotational axis 301 may alternatively be arranged at an angle to the first optical path 202.

Similarly, the second rotatable mount 230 may, as in the present example embodiment, be rotatable about a second rotational axis, which is parallel to the first rotational axis 301, such that, when in the first rotational position 118-1, the second optical element 234 (and the fourth optical element 236) is disposed in the second optical path 203 and, when in the second rotational position 118-2, the second optical element 234 (and the fourth optical element 236) is disposed out of the second optical path 203. The second rotatable mount 230 likewise has a first cuboid axis and a perpendicular second cuboid axis. The second rotatable mount 230 is rotatable about the second rotational axis (in the z-axis direction) such that second cuboid axis is aligned with the second optical path 203 (and the x-axis direction) when the second optical element 224 is at the second rotational position 118-2, and the second cuboid axis is aligned with the second optical path 203 when the second optical element 234 is at the first rotational position 118-1. The second rotational axis is perpendicular to the second optical path 203 (and the entry axis 201). However, the second rotational axis may alternatively be arranged at an angle to the second optical path 203.

Where a fifth optical element is mounted on the first rotatable mount 220 or the second rotatable mount 230, as described above, the optical element mount 210 may further be operable to rotate the fifth optical element such that the fifth optical element is disposed in the first optical path 202 (when mounted on the first rotatable mount 220) or the second optical path 203 (when mounted on the second rotatable mount 230) when the first optical element 224 and the second optical element 234 are at the second rotational position 118-2. For example, the fifth optical element may be supported on either of the third or fourth sides of the hollow cube of the first rotatable mount 220 or the second rotatable mount 230.

Referring to FIGS. 4A and 4B, the first side of the cuboid and the second side of the cuboid each have a respective opening to allow light to propagate along the first optical path 202, through the cuboid and the first optical element 224 and the third optical element 226, when the first optical element 224 and the second optical element 234 are at the first rotational position 118-1. These respective openings are shown along the second axis 303 of the cuboid in FIG. 4B, whereby light may pass through the first optical element 224 and the third optical element 226.

The third side of the cuboid and the opposing fourth side of the cuboid each have a respective opening to allow light to propagate along the first optical path 202, through the cuboid 300 and without passing through any optical element, when the first optical element 224 and the second optical element 234 are at the second rotational position 118-2. These respective openings are shown along the first axis 302 of the cuboid in FIG. 4B, whereby light may pass through the cuboid, only through free space, i.e. without passing through any optical element.

A fifth side of the cuboid and an opposing sixth side of the cuboid are centred on the first rotational axis 301 and may, as in the present example embodiment, comprise protrusions arranged to engage the first rotatable mount 220 with the base plate 290 and the bracket, via ball bearings (or other type of rolling bearing), bushings or other (preferably low friction) coupling. However, these protrusions are optional, and the rotation may be enabled by means differing to those shown. For example, only one of the fifth side or sixth side may comprise a hole or other receptacle to accommodate the axle of the motor 250. Further, the rotational axis need not be centred on the fifth and sixth faces of the cuboid.

The first rotational axis 301 may, as in the present example embodiment, pass through the first optical path 202. Thus, the first optical path 202 may pass through and be parallel to the first cuboid axis 302 when the first optical element 224 and the second optical element 234 are at the second rotational position 118-2, and the first optical path 203 may pass through and be parallel to the second cuboid axis 303 when the first optical element 224 and the second optical element 234 are at the first rotational position 118-1.

The first optical element 224 and the third optical element 226 may, as in the present example embodiment, have different respective masses. Similarly, the second optical element 234 and the fourth optical element 236 may, as in the present example embodiment, have different respective masses. In particular, in the present example embodiment, the polarisers (as examples of the first optical element 224 and second optical element 234) are heavier than the wave plates (as examples of the third optical element 226 and the fourth optical element 236).

The first rotational axis 301 may, as in the present example, be inclined with respect to the direction of the force of gravity acting on the optical element mount 112. As noted above, when the movement mechanism 110 of the present example embodiment is installed in the ophthalmic imaging apparatus 100, the entry axis 201 is parallel (or within 15 degrees of being parallel) to the direction of the force of gravity, and the first rotational axis 302 is perpendicular to the direction of the force of gravity. However, in some example embodiments, the first rotational axis 302 may be parallel to the force of gravity, as described in more detail below.

Where the first rotational axis 301 is inclined with respect to the direction of the force of gravity, the movement mechanism 110 may, as in the present example embodiment, further comprise a counterbalance 310 arranged to reduce (preferably to zero) a resultant moment (torque) about the first rotational axis 301, which comprises a combination of a moment of the first optical element 224 about the first rotational axis 301 and a moment of the third optical element 226 about the first rotational axis 301. In other words, the counterbalance 310 is arranged to reduce (or prevent) a rotation of the first rotatable mount 220 (therefore of the third optical element 226 and the first optical element 224) under action of gravity caused by the difference in the respective moments about the first rotational axis 301 of the third optical element 226 and the first optical element 224. When provided, the counterbalance 310 is, in general, attached to the lighter of the first optical element 224 and the third optical element 226, and has a mass substantially equal to the difference in between of the first optical element 224 and the third optical element 226. As shown in FIGS. 4A and 4B, in the present example embodiment, the counterbalance 310 is mounted adjacent the third optical element 226 such that its centre of mass lies on the second axis 303 of the cuboid. The mass of the counterbalance 310 is selected so that the combined moment about the first rotational axis 301 of the third optical element 226 and the counterbalance 310 equals the moment of the first optical element 224. Accordingly, the torque required by the motor 250 (as an example of actuator 114 in the present example embodiment) is not required to act against a resultant moment (or to act against a small resultant moment) induced by gravity, so that the maximum torque requirement of the motor may be reduced. Further, when the first rotatable mount 220 is at the first rotational position 118-1 or the second rotational position 118-2, the small or zero resultant moment induced by gravity allows the motor 250 can be turned off, or exert only a minimal torque, thereby improving the efficiency of the movement mechanism 110.

As described above, the second rotatable mount 230 is the same as the first rotatable mount 220 in the present example embodiment, as shown in FIGS. 4A and 4B, and includes the same counterbalance. However, the second rotatable mount 230 is rotatable about the second rotational axis which may, as in the present example embodiment, pass through the second optical path 202 and be perpendicular to the second optical path 202, as described above with respect to the first rotational axis 301. The second rotational mount 230 may differ from the first rotational mount 220 by having (or not having) some of the above-described alternatives. The first rotational axis 301 may, as in the present example embodiment, be parallel to the second rotational axis. However, it may alternatively be inclined with respect to the second rotational axis.

Referring again to FIGS. 3A to 3D, the movement mechanism 110 may, as in the present example embodiment, further comprise a mechanical link between first rotatable mount 220 and the second rotatable mount 230. The mechanical link is arranged to cause concurrent rotation of one of the first rotatable mount 220 and the second rotatable mount 230 when the other of the first rotatable mount 220 and the second rotatable mount 240 is rotated. Accordingly, the first rotatable mount 220 and the second rotatable mount 230 can be simultaneously rotated to change the rotational position of the first optical element 224 and the second optical element 234 between the first rotational position 118-1 and the second rotational position 118-2.

The mechanical link may, as in the present example embodiment, be provided in the form of a mechanical arm 240, which connects the fifth face of the first rotatable mount 220 to the fifth face of the second rotational mount 230, as shown in FIGS. 3A and 3C. The mechanical arm 240 can rotate about a respective point to which it is connected (e.g. by a ball joint or the like) on each of the fifth faces, wherein each point is offset from the rotational axis of the respective rotatable mount, preferably by the same amount so that the first rotatable mount 220 and the second rotatable mount 230 rotate in synchronisation with each other (i.e. at the same angular speed). However, the mechanical link may be provided in many other alternative forms, for example in the form of a first gear and a second gear that are arranged to rotate about the first rotational axis 301 and the second rotational axis, respectively, and are coupled together via an intermediate gear that intermeshes with the first and second gear, and causes the first and second gear to rotate in the same sense (i.e. clockwise or anticlockwise). The mechanical link may alternatively be provided in the form of tensioned or toothed belt that mechanically couples a first wheel and a second wheel that are arranged to rotate about the first rotational axis 301 and the second rotational axis, respectively.

Although the optical element mount 112 of the present example embodiment comprises two separate rotatable element mounts that are mechanically coupled so as to rotate synchronously with each other about respective rotational axes that are substantially horizontal, the optical element mount 112 may otherwise be configured to rotate each of the first optical element 224 and the second optical element 234 between a first rotational position 118-1 and a second rotational position 118-2 such that the first optical element 224 is disposed in the first optical path 202 and the second optical element 234 is disposed in the second optical path 203 when the first optical element 224 and the second optical element 234 are in the first rotational position 118-1, and such that the first optical element 224 is disposed out of the first optical path 202 and the second optical element 234 is disposed out of the second optical path 203 when the first optical element 224 and the second optical element 234 are in the second rotational position 118-2.

For example, in a movement mechanism of an alternative embodiment, the optical element mount comprises a rotatable mount arranged to support the first optical element 161 and the second optical element 162, the rotatable mount being rotatable, about a rotational axis perpendicular to the first optical path $P_1$ and the second optical path $P_2$, such that: when at the first rotational position 118-1, the first optical element 161 is disposed in the first optical path $P_1$ and, when at the second rotational position 118-2, the first optical element 161 is disposed out of the first optical path $P_1$; and when at the first rotational position 118-1, the second optical element 162 is disposed in the second optical path $P_2$ and, when at the second rotational position 118-2, the second optical element 162 is disposed out of the second optical path $P_2$. In such alternative embodiment, the actuator 114 is arranged to rotate the rotatable mount about the rotational axis, and the controller 116 is arranged to control the actuator 114 to rotate the rotatable mount such that, when at the first rotational position 118-1, the first optical element 161 is disposed in the first optical path $P_1$ and the second optical element 162 is disposed in the second optical path $P_2$ and, when at the second rotational position 118-2, the first optical element 161 is disposed out of the first optical path $P_1$ and the second optical element 162 is disposed out of the second optical path $P_2$.

In this alternative embodiment, the optical element mount 112 may comprise a hollow cuboid which is arranged to support the first optical element 161 and the second optical element 162 on a first face of the cuboid, and may be further arranged to support the third optical element and the fourth optical element on an opposing second face of the cuboid, wherein the first optical element 161 and the third optical element are mounted on the cuboid, with openings provided in the first and second faces of the cuboid that are aligned with the first and third optical elements such that light can propagate through the cuboid and via the first and third optical elements, along the first optical path $P_1$, when the first optical element 161 and the second optical element 162 are at the first rotational position 118-1. Similarly, the second optical element 162 and the fourth optical element are mounted on the cuboid, with openings provided in the first and second faces of the cuboid that are aligned with the second and fourth optical elements such that light can propagate through the cuboid and via the second and fourth optical elements, along the second optical path $P_2$, when the first optical element 161 and the second optical element 162 are at the second rotational position 118-2. As no mechanical link or hardware for rotationally mounting a second rotational mount is required in this alternative example embodiment, the complexity and parts count of the movement mechanism can be reduced.

When the movement mechanism of the alternative embodiment is installed in the ophthalmic imaging apparatus 100, the optical element mount 112 is operable to rotate the optical elements mounted thereon about a rotational axis which is parallel to the direction of the force of gravity (or inclined with respect to this direction by a small angle, for example an angle smaller than 15 degrees, for example). As a result, the counterbalances of the above example embodiment can be dispensed with, thereby further simplifying the movement mechanism, and reducing its weight. In addition, the consequent decrease in the moment of inertia of the optical element mount 112 about its rotational axis may reduce the delay in switching the optical elements into and out of the optical paths $P_1$ and $P_2$.

Figure 5:
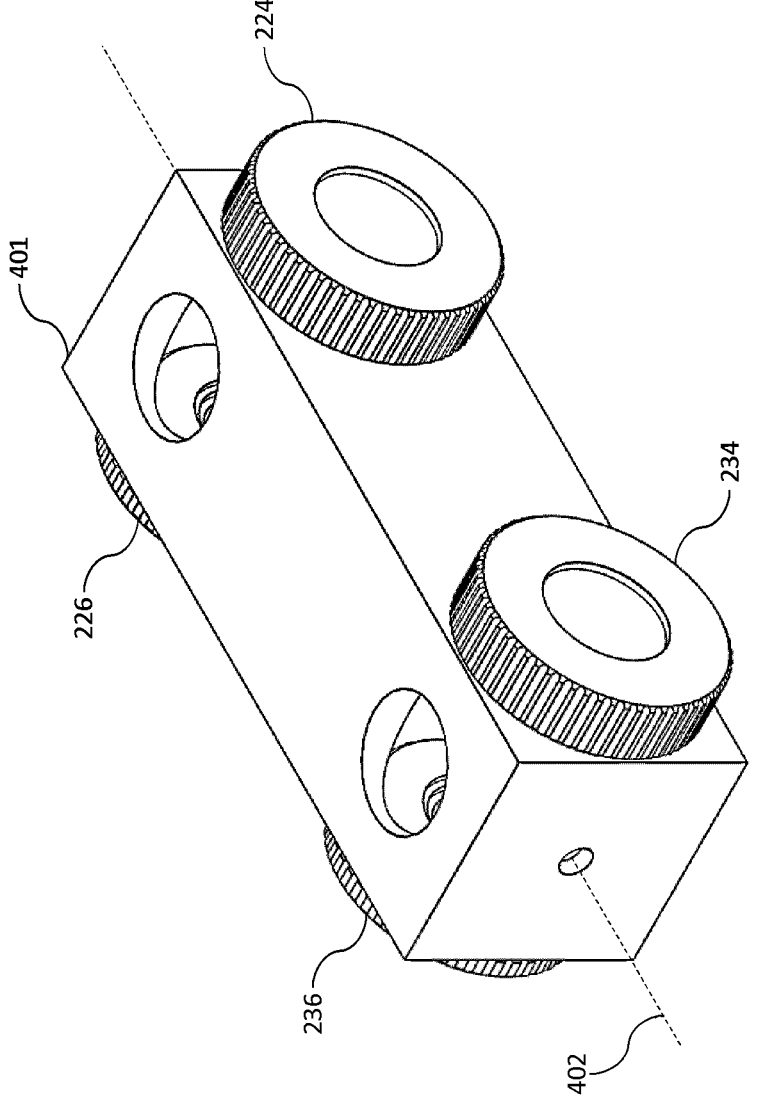
FIG. 5 is an isometric view of an example implementation of the optical element mount 112 in an alternative example embodiment.

FIG. 5 is an isometric view of an example implementation of the optical element mount 112, in accordance with this alternative embodiment. As described above, the optical element mount 112 comprises a hollow cuboid 401, which is arranged to support the first optical element 224 and the second optical element 234 on a first face of the cuboid 401, and is further arranged to support the third optical element 226 and the fourth optical element 236 on an opposing second face of the cuboid 401. The optical element mount 112 is operable to rotate optical elements mounted thereon about a rotational axis 402 which is parallel to the direction of the force of gravity, as described above. The first optical element 224, the second optical element 234, the third optical element 226 and the fourth optical element 236 are as described above with reference to FIGS. 2A to 2D.

Figures 6A, 6B, 6C, 6D:
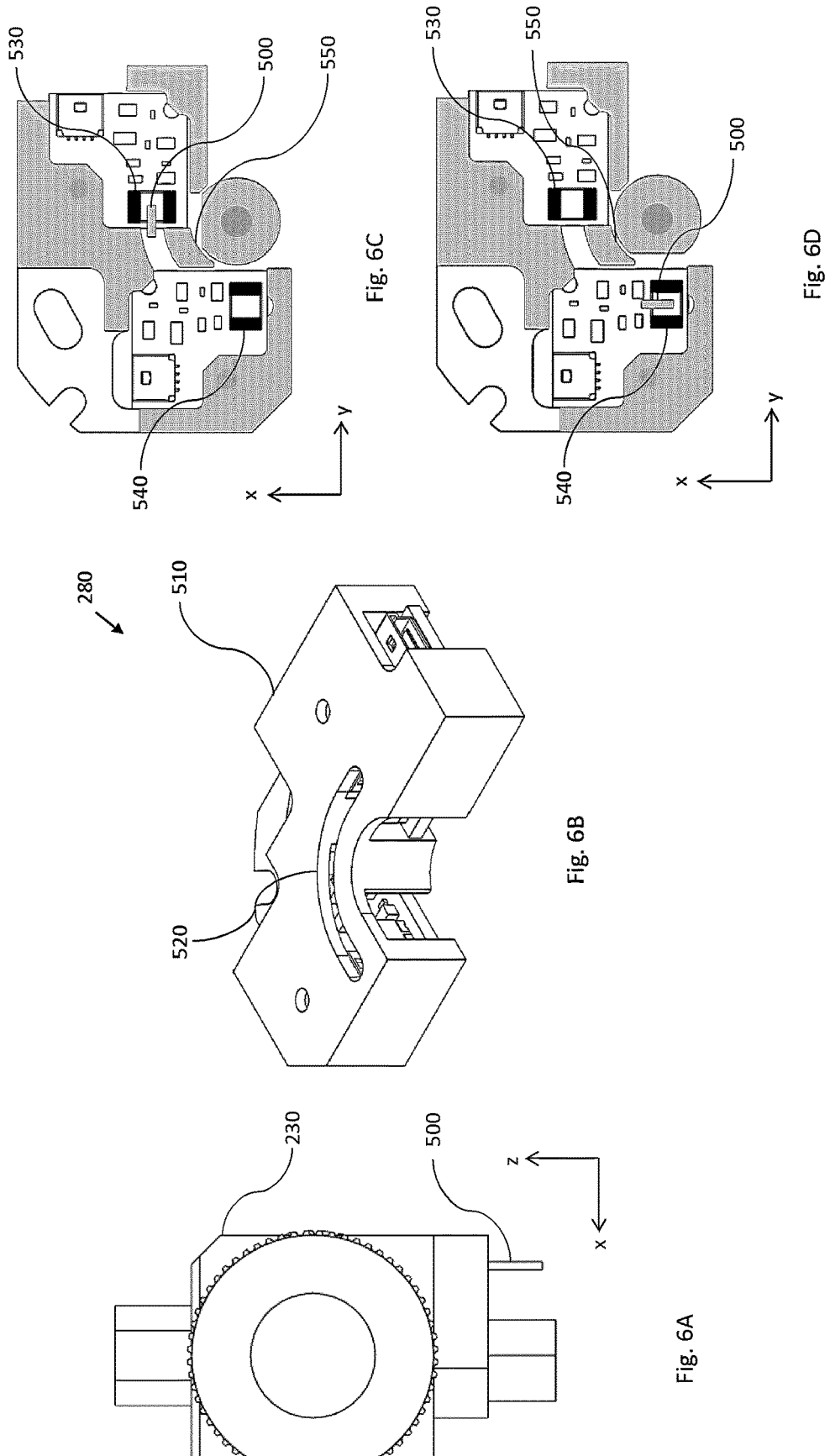
FIG. 6A is a side view of the second rotational mount 230 shown in FIGS. 3A to 3D.
FIG. 6B is an isometric view of the detection module 280 shown in FIGS. 3A to 3D.
FIG. 6C is a cross-sectional view of detection module 280 when protruding part 500 has been rotated into the vicinity of the first optical detector 530.
FIG. 6D is a cross-sectional view of the detection module 280 when protruding part 500 has been rotated in the vicinity of the second optical detector 540.

In the first embodiment or the alternative embodiment described above, the optical element mount 112 may comprise a protruding part, which rotates as the first optical element 234 and the second optical element 236 rotate, so as to move along an arc of a circle. FIG. 6A is a side view of the rotatable mount 230, which shows a protruding part 500 that protrudes from the second rotatable mount 230.

The movement mechanism 110 may further comprise an optical detector. The optical detector is provided within a detection module 280, as shown in FIG. 3B. FIG. 6B shows an enlarged isometric view of detection module 280. FIGS. 6C and 6D are cross-sectional views in the x-y plane of the detection module 280, which illustrate a first optical detector 530 and a second optical detector 540 of the detection module 280. The first optical detector 530 may, as in the present example embodiment, be arranged to detect the protruding part 500 when the protruding part 500 is rotated into a vicinity of (i.e. within a predetermined distance from, or within a predefined range of locations relative to) the first optical detector 530 during rotation of the first optical element 224 and the second optical element 234, the first optical detector 530 being disposed in the movement mechanism 110 such that a detection of the protruding part 500 indicates that the first optical element 224 and the second optical element 234 are at the first rotational position 118-1. The first optical detector 530 may, as in the present example embodiment, be arranged to emit a beam of light across a gap, which can be blocked by the protruding part 500, specifically when the second optical element 234 mounted on the second rotatable mount 230 is at the first rotational position 118-1, as in the case of FIGS. 3A and 3B. However, any other optical detector arrangement may be used, which can indicate the presence of the protruding part 500 when the first optical element 224 and the second optical element 234 are at the first rotational position 118-1.

The second optical detector 540 may be similarly arranged to the first optical detector 530, to detect the protruding part 500 when the protruding part 500 is rotated into a vicinity of the second optical detector 540 during rotation of the first optical element 224 and the second optical element 234, wherein the second optical detector 530 is disposed in the movement mechanism 110 such that a detection of the protruding part 500 indicates that the first optical element 224 and the second optical element 234 are at the second rotational position. In FIG. 6D, the first optical detector 530 emits a beam of light across a gap, which can be blocked by the protruding part 500, specifically when the second optical element 234 mounted on the second rotatable mount 230 is at the second rotational position 118-2, as in the case of FIGS. 3C and 3D. However, any optical detector arrangement may be used that can indicate the presence of the protruding part 500 when the second optical element 234 is at the second rotational position 118-2.

The movement mechanism 110 may further comprise a housing 510 for the optical detectors 530 and 540, as illustrated in FIG. 6B. The housing 510 is provided with an arcuate slit 520 to allow the protruding part 500 to move along an arc of a circle between the first optical detector 530 and the second optical detector 540. The housing 510 may, as in the present example embodiment, be arranged to surround the first optical detector 530 and the second optical detector 540 so as to prevent (or at least suppress) an egress of light from the first optical detector 530 and the second optical detector 540 to an exterior of the housing 510. The housing 510 may be further arranged to prevent (or at least suppress) propagation of light between the first optical detector 530 and the second optical detector 540. The housing 510 thus surrounds the first optical detector 530 and the second optical detector 540 so as to reduce (preferably minimise) the amount of light which can escape from the housing 510. Further, as illustrated in FIGS. 6C and 6D, a portion 550 of the housing 510 may be provided to block the passage of light between the first optical detector 530 and the second optical detector 540. By suppressing the escape of light from the first optical detector 530 and the second optical detector 540 to the exterior of the housing 510, interference with the first light $L_1$ and the second light $L_2$ of the ophthalmic imaging apparatus 100 can be avoided, thus ultimately allowing image quality of the ophthalmic imaging apparatus 100 to be improved through reduced signal-to-noise in photodetection. Further, by preventing crosstalk between the first optical detector 530 and the second optical detector 540, the reliability of the indications of the current rotational position can be improved.

The first optical detector 520 and the second optical detector 530 may, as in the present example embodiment, both be attached to the housing 510. More specifically, in the present example embodiment, the optical detectors 520 and 530 are attached to a printed circuit board, which is attached to the housing 510. However, the optical detectors 530 and 540 may alternatively be attached directly to the housing 510. The housing 510 may, as in the present example embodiment, be detachable from the movement mechanism 110. The housing 510 may, for example, be attached to the base plate 290 using screws passing through the housing and into the base plate 290. The first optical detector 530 and the second optical detector 540 can thus easily be removed from the mount 200 and adjusted, repaired or replaced, thus improving the serviceability of the ophthalmic imaging apparatus 100.

Although the detection module 280 has been described above to interact with a protruding part 500 of the second rotatable mount 230, another arrangement may alternatively be adopted, depending on the arrangement of the optical element mount 160. For example, where, as described above, the optical element mount 112 comprises a single rotatable mount in the form of a hollow cuboid to support all four optical elements, the protruding part may be placed on the lower end of the described hollow cuboid. As the rotational axis in this case would be parallel to the entry axis 201, the detection element may be placed on a bracket under the lower end of the hollow cuboid, such that the protruding part can rotate along the arc of the circle along which it travels between the first optical detector 530 and second optical detector 540.

Furthermore, the aforementioned optical detectors may be replaced with any kind of proximity detector that is capable of detecting when the protruding part 500 comes into the vicinity of the detector without physical contact between the detector and the protruding part 500. The proximity detector may, for example, be a capacitive proximity detector or an inductive proximity detector. Alternatively, the aforementioned optical detectors may be replaced with mechanical detectors (such as microswitches, for example), which rely on physical contact between the detector and the protruding part 500 for detection of the protruding part 500. For example, a mechanical switch may be arranged to detect the protruding part 500 when the protruding part 500 is rotated such that it activates the mechanical switch during rotation of the first optical element 224 and the second optical element 234. Where the mechanical switch replaces the first optical detector 530, the mechanical switch is disposed in the movement mechanism 110 such that a detection of the protruding part 500 indicates that the first optical element 224 and the second optical element 234 are at the first rotational position 118-1. Where two detectors are provided to determine the rotational position of the first optical element 224 and the second optical element 234 (and any further supported optical elements), as described above, the detector types of these detectors may be the same or any combination of the different types set out above. Furthermore, in example embodiments comprising one or more detectors arranged to detect the protruding part in their vicinity, which are not optical detectors, the housing 510 may be omitted (unless required for a purpose other than to block light, for example to act as a dust cover).

Referring again to FIG. 1, the actuator 114 is arranged to drive the optical element mount 112 so as to set the first optical element 161 and the second optical element 162 to the first rotational position 118-1 or the second rotational position 118-2. The actuator 114 may, as in the present example embodiment, be provided in the form of the motor 250 shown in FIGS. 3A to 3D, which is arranged to rotate the second rotatable mount 230 about the second rotational axis. However, the actuator 114 may alternatively be arranged to rotate the first rotatable mount 220 about the first rotational axis 301, with the mechanical link 240 causing the second rotatable mount 230 to rotate in synchronisation with the first rotational mount 220. The motor 250 is secured to the bracket of the optical element mount 210 such that its axle is aligned with the second rotational axis and coupled to the second rotatable mount 230. However, other arrangements are possible. For example, the motor may instead be secured to an underside of the base plate 290 but otherwise configured in the same way to drive the second rotatable mount 230. Although the actuator 114 takes the form of an electric motor 250 in the present example embodiment, any other drive system for causing the rotatable mounts to rotate may alternatively be used, such as a linear motor and a mechanical arrangement to convert linear drive of the linear motor to a rotation of the first rotatable mount 220 or the second rotatable mount 230.

The controller 116 is arranged to control the actuator 114 to set the rotational position of the first optical element 161 and the second optical element 162 to the first rotational position 118-1 when the ophthalmic imaging apparatus 100 is operating in the first imaging mode, and to the second rotational position 118-2 when the ophthalmic imaging apparatus 100 is operating in the second imaging mode. The controller 116 may, as in the present example embodiment, be arranged to control the actuator 114 to rotate one of the first rotatable mount 220 and the second rotatable mount 230 such that, when at the first rotational position 118-1, the first optical element 161 is disposed in the first optical path $P_1$ and the second optical element 162 is disposed in the second optical path $P_2$ and, when at the second rotational position 118-2, the first optical element 161 is disposed out of the first optical path $P_1$ and the second optical element 162 is disposed out of the second optical path $P_2$.

The first imaging mode of the ophthalmic imaging apparatus 110 may, as in the present example embodiment, be a colour imaging mode, while the second imaging mode is autofluorescence. Accordingly, when the ophthalmic imaging apparatus 100 operates in the colour imaging mode, the combination of a polariser and a quarter wave plate is placed into each of the first optical path $P_1$ and second optical path $P_2$. However, when operating in the AF imaging mode, the polarisers and quarter wave plates are rotated out of the first and second optical paths to prevent unwanted attenuation of the first light $L_1$ and the second light $L_2$, which tend to be relatively low-level signals in the AF mode.

The above-described movement mechanism 110 may also be advantageous for other imaging modes of the ophthalmic imaging apparatus 100. For example, the first imaging mode of the ophthalmic imaging apparatus 100 may be OCT that employs IR SLO eye tracking and the second imaging mode of the ophthalmic imaging apparatus 100 may be ICG angiography. In such a case, the above-described fifth optical element, comprising an IR filter, may be required in the second (red) optical path $P_2$ for the ICG angiography imaging mode. However, in the first imaging mode, this IR filter is preferably removed for the IR SLO eye tracking, and a polariser and a quarter wave plate should instead be included, and this change of optical elements in the second optical path $P_2$ may be achieved by the movement mechanism 110, as described above.

FIG. 7 is a flow diagram illustrating a computer-implemented method of controlling movement of optical elements into and out of respective optical paths in the ophthalmic imaging apparatus 100 of the first example embodiment, according to a second example embodiment. Elements described in the following method steps with the same reference numerals as described in the foregoing description are the same, the description of which will not be repeated here. The method is performed by controller 116, which, as described above, can control the operation of the movement mechanism 110, specifically by controlling the actuator 114, which is arranged to drive the optical element mount 112. The controller 116 may comprise a storage device storing computer-readable instructions and a processor, wherein the instructions, when executed by the processor, cause the processor to perform the method described herein with reference to FIG. 7.

In S10 of FIG. 7, the controller 116 determines, for example based on a command provided by a user via an input device (e.g. a keyboard) or based on a predetermined schedule (stored in the storage device or otherwise made available to the processor), whether the ophthalmic imaging apparatus 100 is to switch from operating in the first imaging mode to operating in the second imaging mode.

In S20 of FIG. 7, the controller 116, in response to determining that the ophthalmic imaging apparatus 100 is to switch from operating in the first imaging mode to operating in the second imaging mode, generates control signals to cause the first optical element 161 and the second optical element 162 to be concurrently rotated (e.g. by the actuator 114 of the above example embodiment) to a second rotational position 118-2 such that the first optical element 161 is disposed out of the first optical path $P_1$ and the second optical element 162 is disposed out of the second optical path $P_2$.

In S30 of FIG. 7, the controller 116 determines, based on a command provided by a user via an input device (e.g. a keyboard) or based on a predetermined schedule, for example, whether the ophthalmic imaging apparatus 100 is to switch from operating in the second imaging mode to operating in the first imaging mode.

In S40 of FIG. 7, the controller 116, in response to determining that the ophthalmic imaging apparatus 100 is to switch from operating in the second imaging mode to operating in the first imaging mode, generates control signals to cause the first optical element 161 and the second optical element 162 to be concurrently rotated (e.g. by the actuator 114 of the above example embodiment) to a first rotational position 118-1 such that the first optical element 161 is disposed in the first optical path $P_1$ and the second optical element 162 is disposed in the second optical path $P_2$.

While S10 to S40 of FIG. 7 are described in a particular order, the computer-implemented method described above is not so limited. For example, S30 and S40 may be performed before S10 and S20.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Some aspects of the examples presented herein, such as the function of the controller 116, may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some or all of the functionality of the controller may also be implemented by the preparation of application-specific integrated circuits, field-programmable gate arrays, or by interconnecting an appropriate network of conventional component circuits.

A computer program product may be provided in the form of a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, RAID, a remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The invention claimed is:

1. An ophthalmic imaging apparatus operable in a first imaging mode and a second imaging mode to acquire images of a portion of an eye, the ophthalmic imaging apparatus comprising:
   a light source;
   a photodetector;
   an optical system arranged to illuminate the portion of the eye with light from the light source and collect light from the illuminated portion of the eye, the optical system being further arranged to split the collected light into a first light and a second light, and convey guide the first light towards the photodetector via a first optical path, and the second light to the photodetector via a second optical path, the first optical path being different from the second optical path; and,
   a movement mechanism arranged to move a first optical element into and out of the first optical path, and concurrently move a second optical element into and out of the second optical path, wherein the first optical path and the second optical path pass through the movement mechanism, the movement mechanism comprising:
      an optical element mount arranged to support the first optical element and the second optical element, the optical element mount being operable to rotate each of the first optical element and the second optical element between a first rotational position and a second rotational position such that:

the first optical element is disposed in the first optical path and the second optical element is disposed in the second optical path when the first optical element and the second optical element are in the first rotational position; and the first optical element is disposed out of the first optical path and the second optical element is disposed out of the second optical path when the first optical element and the second optical element are in the second rotational position;

an actuator arranged to drive the optical element mount so as to set the first optical element and the second optical element to the first rotational position or the second rotational position; and a controller arranged to control the actuator to set the rotational position of the first optical element and the second optical element to the first rotational position when the ophthalmic imaging apparatus is operating in the first imaging mode, and to the second rotational position when the ophthalmic imaging apparatus is operating in the second imaging mode.

2. The ophthalmic imaging apparatus according to claim 1, wherein:

the optical element mount comprises:

a first rotatable mount arranged to support the first optical element, the first rotatable mount being rotatable, about a first rotational axis, such that, when at the first rotational position, the first optical element is disposed in the first optical path and, when in the second rotational position, the first optical element is disposed out of the first optical path; and a second rotatable mount arranged to support the second optical element, the second rotatable mount being rotatable, about a second rotational axis, such that, when at the first rotational position, the second optical element is disposed in the second optical path and, when in the second rotational position, the second optical element is disposed out of the second optical path, wherein the first rotational axis is parallel to the second rotational axis, the first rotational axis is perpendicular to the first optical path, and the second rotational axis is perpendicular to the second optical path, the movement mechanism further comprises a mechanical link between first rotatable mount and the second rotatable mount, the mechanical link being arranged to cause concurrent rotation of one of the first rotatable mount and the second rotatable mount when the other of the first rotatable mount and the second rotatable mount is rotated, the actuator is arranged to rotate one of the first rotatable mount and the second rotatable mount about the respective one of the first rotational axis and the second rotational axis, and the controller is arranged to control the actuator to rotate the one of the first rotatable mount and the second rotatable mount such that, when at the first rotational position, the first optical element is disposed in the first optical path and the second optical element is disposed in the second optical path and, when at the second rotational position, the first optical element is disposed out of the first optical path and the second optical element is disposed out of the second optical path.

3. The ophthalmic imaging apparatus according to claim 2, wherein the first rotational axis and the second rotational axis pass through the first optical path and the second optical path, respectively.

4. The ophthalmic imaging apparatus according to claim 2, wherein the movement mechanism is further arranged to, when moving the first optical element into and out of the first optical path and concurrently moving the second optical element into and out of the second optical path, concurrently move a third optical element into and out of the first optical path, by the optical element mount being further arranged to support the third optical element and rotate the third optical element such that the third optical element is disposed in the first optical path when the first optical element and the second optical element are at the first rotational position, and such that the third optical element is disposed out of the first optical path when the first optical element and the second optical element are at the second rotational position.

5. The ophthalmic imaging apparatus according to claim 4, wherein:

the first rotatable mount comprises a hollow cuboid arranged to support the first optical element on a first side of the cuboid, and arranged to support the third optical element on an opposing second side of the cuboid, each of the first side of the cuboid and the second side of the cuboid each has a respective opening to allow light to propagate along the first optical path, through the cuboid and the first and third optical elements, when the first optical element and the second optical element are at the first rotational position, and each of a third side of the cuboid and an opposing fourth side of the cuboid each has a respective opening to allow light to propagate along the first optical path, through the cuboid and without passing through any optical element, when the first optical element and the second optical element are at the second rotational position.

6. The ophthalmic imaging apparatus according to claim 5, wherein the movement mechanism further comprises the first optical element and the third optical element, wherein the first optical element comprises a polariser, and the third optical element comprises a wave plate.

7. The ophthalmic imaging apparatus according to claim 4, wherein the optical element mount further comprises the first optical element and the third optical element, the optical element mount being operable to rotate the first optical element and the third optical element about a rotational axis which is inclined with respect to a direction of a force of gravity acting on the optical element mount, the first optical element and the third optical element having different respective moments about the rotational axis, wherein the movement mechanism further comprises a counter-balance arranged to reduce a resultant moment about the rotational axis, the resultant moment comprising a combination of the moment of the first optical element about the rotational axis and the moment of the third optical element about the rotational axis.

8. The ophthalmic imaging apparatus according to claim 4, wherein the third optical element is rotatably mounted on the optical element mount so as to be manually rotatable about the optical element mount.

9. The ophthalmic imaging apparatus according to claim 1, wherein:

the optical element mount comprises a rotatable mount arranged to support the first optical element and the second optical element, the rotatable mount being rotatable, about a rotational axis perpendicular to the first optical path and the second optical path, such that:

when at the first rotational position, the first optical element is disposed in the first optical path and, when at the second rotational position, the first optical element is disposed out of the first optical path; and when at the first rotational position, the second optical element is disposed in the second optical path and, when at the second rotational position, the second optical element is disposed out of the second optical path, the actuator is arranged to rotate the rotatable mount about the rotational axis, and the controller is arranged to control the actuator to rotate the rotatable mount such that, when at the first rotational position, the first optical element is disposed in the first optical path and the second optical element is disposed in the second optical path and, when at the second rotational position, the first optical element is disposed out of the first optical path and the second optical element is disposed out of the second optical path.

10. The ophthalmic imaging apparatus according to claim 1, wherein at least one of the first optical element and the second optical element is rotatably mounted on the optical element mount so as to be manually rotatable about the optical element mount.

11. The ophthalmic imaging apparatus according to claim 1, wherein:

the optical element mount comprises a protruding part arranged to rotate with rotation of the first optical element and the second optical element so as to move along an arc of a circle, and the movement mechanism further comprises:

an optical detector arranged to detect the protruding part when the protruding part is rotated into a vicinity of the optical detector during rotation of the first optical element and the second optical element, the optical detector being disposed in the movement mechanism such that a detection of the protruding part by the optical detector indicates that the first optical element and the second optical element are at one of the first rotational position and the second rotational position; and a housing for the optical detector, the housing being arranged to surround the optical detector so as to suppress an egress of light from the optical detector to an exterior of the housing.

12. The ophthalmic imaging apparatus according to claim 11, wherein:

the optical detector is a first optical detector, and the movement mechanism further comprises a second optical detector arranged to detect the protruding part when the protruding part is rotated into a vicinity of the second optical detector during rotation of the first optical element and the second optical element, the second optical detector being disposed in the movement mechanism such that a detection of the protruding part by the second optical detector indicates that the first optical element and the second optical element are at the other of the first rotational position and the second rotational position, and the housing is further arranged to surround the second optical detector so as to suppress an egress of light from the second optical detector to the exterior of the housing, the housing being further arranged to suppress propagation of light between the first optical detector and the second optical detector.

13. The ophthalmic imaging apparatus according to claim 11, wherein the optical detector is attached to the housing, the housing being detachable from the movement mechanism.

14. The ophthalmic imaging apparatus according to claim 1, wherein:

the first imaging mode is a reflectance imaging mode, wherein the ophthalmic imaging apparatus acquires a reflectance image of the eye, the second imaging mode is a fluorescence imaging mode, wherein the ophthalmic imaging apparatus acquires a fluorescence image of the eye, and each of the first optical element and the second optical element comprises a polariser.

\* \* \* \* \*